United States Patent [19]

Cipolli et al.

[11] Patent Number: 5,296,598
[45] Date of Patent: Mar. 22, 1994

[54] DERIVATIVES OF 2,4-DIAMINO-1,3,5-TRIAZINYL-6-PHOSPHONIC ACID

[75] Inventors: Roberto Cipolli, Novara; Enrico Masarati, Castelnuovo Valtidone; Cristina Rossi, Rome; Roberto Oriani, Milan; Gilberto Nucida, San Giuliano Milanese, all of Italy

[73] Assignee: Ministero dell'Universita' e della Ricerca Scientifica e Technologica, Rome, Italy

[21] Appl. No.: 1,528

[22] Filed: Jan. 6, 1993

[30] Foreign Application Priority Data

Jan. 10, 1992 [IT] Italy ............................ MI92A000018

[51] Int. Cl.$^5$ .................... C07D 251/40; C07F 9/53
[52] U.S. Cl. ................................. 544/195; 544/60; 544/84; 544/113; 544/69; 544/57; 534/617; 534/799
[58] Field of Search ................ 544/195, 60, 84, 113, 544/69, 57; 534/617, 799

[56] References Cited

U.S. PATENT DOCUMENTS 3,213,093 10/1965 Papp et al. ................... 200/249.8

FOREIGN PATENT DOCUMENTS 0415371 3/1991 European Pat. Off. .
0466137 1/1992 European Pat. Off. .
2295042 7/1976 France .

Primary Examiner—John M. Ford
Attorney, Agent, or Firm—Oblon, Spivak, McClelland, Maier & Neustadt

[57] ABSTRACT

Derivatives of triazinylphosphonic acid having the general formula (I):

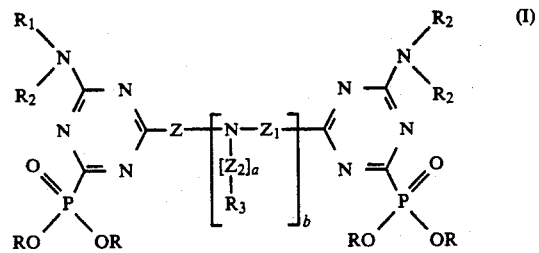

obtained by means of the reaction of condensation of a cyanuric halide with an ester of phosphorous acid and subsequent reaction of substitution with a polyamine and an amine.

7 Claims, No Drawings

DERIVATIVES OF 2,4-DIAMINO-1,3,5-TRIAZINYL-6-PHOSPHONIC ACID

The present invention relates to phosphonic esters and acids of triazinic derivatives.

More particularly, the present invention relates to derivatives of 2,4-diamino-1,3,5-triazinyl-6-phosphonic acid.

These compounds find use in the preparation of self-extinguishing compositions based on thermoplastic polymers, or on polymers endowed with elastomeric properties, in particular olefinic polymers or copolymers, either atone, or together with small amounts of ammonium or amine phosphates and/or phosphonates.

In particular, the subject matter of the present invention are the compounds having the general formula (I):

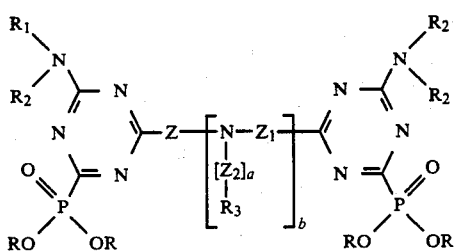

wherein
the radicals R, which may be the same, or different from each other, are: hydrogen; $C_1-C_5$ alkyl; $C_3-C_5$ hydroxyalkyl; $C_3-C_4$ alkenyl; cyclohexyl; $C_6-C_{10}$ aryl; $C_7-C_8$ aralkyl; or, taken jointly, may constitute a cyclic structure, as:

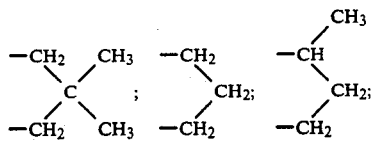

the radicals $R_1$ and $R_2$, which may be the same, or different from each other, and which may have different meanings on each triazinic ring, are: H; $C_1-C_{18}$ alkyl; $C_2-C_8$ alkenyl; $C_6-C_{16}$ cycloalkyl or alkylcycloalkyl;

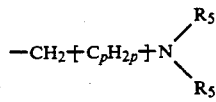

wherein:
m = an integer comprised within the range of from 1 to 7;
p = an integer comprised within the range of from 1 to 5;
$R_4$ = H; $C_1-C_8$ alkyl; $C_2-C_6$ alkenyl; $+C_qH_{2q}+O-R_6$ wherein q is an integer comprised within the range of from 1 to 4 and $R_6$ is H or $C_1-C_4$ alkyl; $C_6-C_{12}$ cycloalkyl or alkylcycloalkyl;
the radicals $R_5$, which may be the same, or different from each other, are: H; $C_1-C_8$ alkyl; $C_2-C_6$ alkenyl; $C_6-C_{12}$ cycloalkyl or alkylcycloalkyl; $C_1-C_4$ hydroxyalkyl; or the moiety:

is replaced by a heterocyclic radical linked to the alkyl chain through the nitrogen atom, and possibily containing another heteroatom preferably selected from O, S, N;
or in the general formula (I) the moiety:

is replaced by a heterocyclic radical linked to the triazinic ring through the nitrogen atom, and possibly containing another heteroatom preferably selected from O, S, N;
a is 0 (zero) or 1;
b is 0 (zero) or an integer comprised within the range of from 1 to 5;
$R_3$ is hydrogen or:

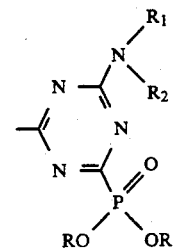

and its meaning may vary within each repeating unit; when b is 0 (zero), Z is a divalent radical falling within the scope of one of the following formulae:

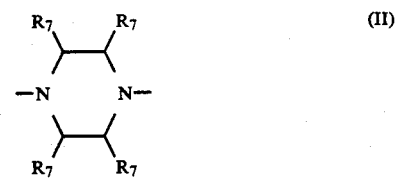

wherein the radicals $R_7$, which may be the same or different from each other, are hydrogen or $C_1-C_4$ alkyl;

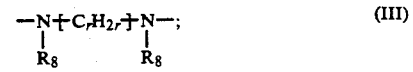

wherein r is an integer comprised within the range of from 2 to 14; $R_8$ is hydrogen; $C_1-C_4$ alkyl; $C_2-C_6$ alkenyl; $C_1-C_4$ hydroxyalkyl;

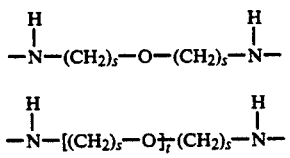 (V)

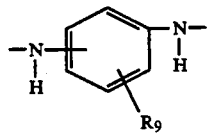 (VI)

wherein s is an integer comprised within the range of from 2 to 5 and t is an integer comprised within the range of from 1 to 3;

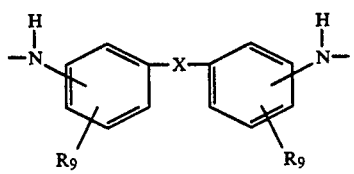 (VII)

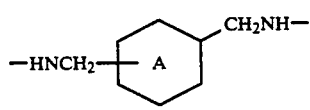 (VIII)

wherein:
X is a direct C—C bond; O; S; S—S; SO; $SO_2$; NH; $NHSO_2$; NHCO; N=N; $CH_2$;
$R_9$ is hydrogen; hydroxy; $C_1$-$C_4$ alkyl; $C_1$-$C_4$ alkoxy;

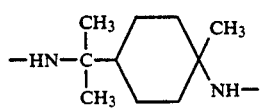 (IX)

wherein A may be a saturated or unsaturated ring;

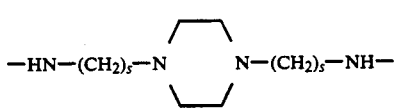 (X)

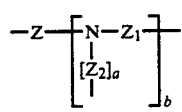 (XI)

wherein s has the above defined meaning;
when, on the contrary, b is an integer comprised within the range of from 1 to 5, the moiety:

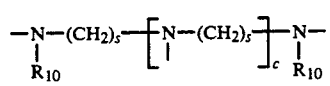

is a multivalent radical falling within the scope of one of the following formulae:

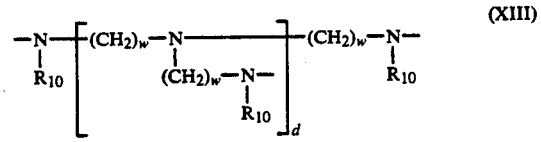 (XII)

wherein:
$R_{10}$ is hydrogen or $C_1$-$C_4$ alkyl;
c is an integer comprised within the range of from 1 to 5;
the indexes s, which may be the same, or different from each other, have the same meaning as defined hereinabove;

 (XIII)

wherein:
$R_{10}$ has the same meaning as defined hereinabove;
w is an integer comprised within the range of from 2 to 4;
d is either 1 or 2.

Within the scope of general formula (I) also those derivatives fall which have an asymmetrical structure, in the sense that the radicals $R_1$ and $R_2$ may have different meanings on each triazinic derivative.

Examples of radicals R in the general formula (I) are: methyl; ethyl; propyl; isopropyl; n-butyl; isobutyl; isopentyl; 3-hydroxypropyl; 3-hydroxy-3-methylpropyl; 3-hydroxy-2,2-dimethylpropyl; propenyl; butenyl; cyclohexyl; phenyl; 2-methylphenyl; 3-methylphenyl; 4-methylphenyl; 2,6-dimethylphenyl; 4-isopropylphenyl; 4-tert-butylphenyl; benzyl; 1-phenylethyl; and so forth.

Examples of radicals $R_1$ and $R_2$ are: methyl; ethyl; propyl; isopropyl; n-butyl; isobutyl; tert-butyl; n-pentyl; isopentyl; n-hexyl; tert-hexyl; octyl; tert-octyl; decyl; dodecyl; octadecyl; ethenyl; propenyl; butenyl; isobutenyl; hexenyl; octenyl; cyclohexyl; propylcyclohexyl; butylcyclohexyl; decylcylohexyl; hydroxycyclohexyl; hydroxyethylcyclohexyl; 2-hydroxyethyl; 2-hydroxypropyl; 3-hydroxypropyl; 3-hydroxybutyl; 4-hydroxybutyl; 3-hydroxypentyl; 5-hydroxypentyl; 6-hydroxyhexyl; 3-hydroxy-2,5-dimethylhexyl; 7-hydroxyheptyl; 7-hydroxyoctyl; 2-methoxyethyl; 2-methoxypropyl; 3-methoxypropyl; 4-methoxybutyl; 6-methoxyhexyl; 7-methoxyheptyl; 7-methoxyoctyl; 2-ethoxyethyl; 3-ethoxypropyl; 4-ethoxybutyl; 3-propoxypropyl; 3-butoxypropyl; 4-butoxybutyl; 4-isobutoxybutyl; 5-propoxypentyl; 2-cyclohexyloxyethyl; 2-ethenyloxyethyl; 2-(N,N-dimethylamino)ethyl; 3-(N,N-dimethylamino)propyl; 4-(N,N-dimethylamino)butyl; 5-(N,N-dimethylamino)pentyl; 4-(N,N-diethylamino)butyl; 5-(N,N-diethylamino)pentyl; 5-(N,N-diisopropylamino)pentyl; 3-(N-ethylamino)propyl; 4-(N-methylamino)butyl; 4-(N,N-dipropylamino)butyl; 2-(N,N-diisopropylamino)ethyl; 6-(N-hexenylamino)hexyl; 2-(N-ethenylamino)ethyl; 2-(N-cyclohexylamino)ethyl; 2-(N-2hydroxyethylamino)ethyl; 2-(2-hydroxyethoxy)ethyl; 2-(2-methoxyethoxy)ethyl; 6-(N-propylamino)hexyl; and so forth. Examples of heterocyclic radicals which may replace the moiety:

$$-N\begin{matrix}R_1\\R_2\end{matrix}$$

in general formula (I) are: aziridine; pyrrolidine; piperidine; morpholine; thiomorpholine; piperazine; 4- methylpiperazine; 4-ethylpiperazine; 2-methylpiperazine; 2,5-dimethylpiperazine; 2,3,5,6-tetramethylpiperazine; 2,2,5,5-tetramethylpiperazine; 2-ethylpiperazine; 2,5-diethylpiperazine; and so forth.

Examples of heterocyclic radicals which may replace the moiety:

are: aziridine; pyrrolidine; piperidine; morpholine; thiomorpholine; piperazine; 4-methylpiperazine; 4-ethylpiperazine; and so forth.

Examples of divalent —Z— radicals are those which derive, by means of the removal of a hydrogen atom from each aminic group, from the following diaminic compounds: piperazine; 2-methylpiperazine; 2,5-dimethylpiperazine; 2,3,5,6-tetramethylpiperazine; 2-ethylpiperazine; 2,5-diethylpiperazine; 1,2-diaminoethane; 1,3-diaminopropane; 1,4-diaminobutane; 1,5-diaminopentane; 1,6-diaminohexane; 1,8-diaminooctane; 1,10-diaminodecane; 1,12-diaminododecane; N,N'-dimethyl-1,2-diaminoethane; N-methyl-1,3-diaminopropane; N-ethyl- 1,2-diaminoethane; N-isopropyl-1,2-diaminoethane; N-(2-hydroxyethyl)-1,2-diaminoethane; N,N'-bis(2-hydroxyethyl)-1,2-diaminoethane; N-(2-hydroxyethyl)-1,3-diaminopropane; N-hexenyl-1,6-diaminohexane; N,N'-diethyl-1,4-diamino-2-butene; 2,5-diamino-3-hexene; 2-aminoethylether; (2-aminoethoxy)-methylether; 1,2-bis(2-aminoethoxy)ethane; 1,3-diaminobenzene; 1,4-diaminobenzene; 2,4-diaminotoluene; 2,4-diaminoanisole; 2,4-diaminophenol; 4-aminophenylether; 4,4'-methylenedianiline; 4,4'-diaminobenzanilide; 3-aminophenylsulfone; 4-aminophenylsulfone; 4-aminophenylsulfoxide; 4-aminophenyldisulfide; 1,3-bis(aminomethyl)benzene; 1,4-bis(aminomethyl)benzene; 1,3-bis(aminomethyl)cyclohexane; 1,8-diamino-p-mentane; 1,4-bis(2-aminoethyl)piperazine; 1,4-bis(3-aminopropyl)piperazine; 1,4-bis(4-aminobutyl)piperazine; 1,4-bis(5-aminopentyl)piperazine; and so forth.

Examples of multivalent radicals:

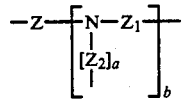

are those which derive, by elimination of a hydrogen atom from each reacted amino group, from the following polyaminic compounds: bis(2-aminoethyl)amine; bis(3-aminopropyl)amine; bis(4-aminobutyl)amine; bis(5-aminopentyl)amine; bis[2-(N-methylamino)ethyl]amine; 2-N-butyl-bis(2-aminoethyl)amine; bis[3-(N-methylamino)propyl]amine; N-(3-aminopropyl)-1,4-diaminobutane; N-(3-aminopropyl)-1,5-diaminopentane; N-(4-aminobutyl)-1,5-diaminopentane; tris(2-aminoethyl)amine; tris(3-aminopropyl)amine; tris(4-aminobutyl)amine; tris[2-(N-ethylamino)ethyl]amine; N,N'-bis(2-aminoethyl)-1,2-diaminoethane; N,N'-bis(3-aminopropyl)-1,3-diaminopropane; N,N'-bis(2-aminoethyl)-1,3-diaminopropane; N,N'-bis(3-aminopropyl)-1,2-diaminopropane; N,N'-bis(3-aminopropyl)-1,4-diaminobutane; bis[2-(2-aminoethyl)aminoethyl]amine; N,N'-bis[2-(2-aminoethyl)aminoethyl]-1,2-diaminoethane; N,N'-bis[3-(2-aminoethyl)aminopropyl]-1,2-diaminoethane; N,N,N',N'-tetrakis(2-aminoethyl)-1,2-diaminoethane; and so forth.

Specific compounds falling within the scope of the general formula (I) are reported in the examples which follow the present disclosure.

The derivatives of triazinylphosphonic acid of general formula (1) in which the radicals R are different from hydrogen or $C_3$-$C_5$ hydroxyalkyl, can be synthetized by causing a cyanuric halide, e.g., cyanuric chloride, to react, at a temperature comprised within the range of from 0° to 200° C., in the presence, or less, of a suitable solvent (such as, e.g., acetone, toluene, xylene, and so forth) with a phosphite having the general formula (XIV):

$$P(OR)_3 \qquad (XIV)$$

wherein R has the meaning as defined hereinabove (except for hydrogen and $C_3$-$C_5$ hydroxyalkyl), in order to yield the intermediate having the general formula (XV):

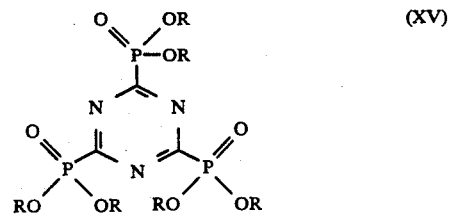

Examples of phosphite are: trimethylphosphite; triethylphosphite; tripropylphosphite; triisopropylphosphite; tributylphosphite; triisobutylphosphite; triisopentylphosphite; triallylphosphite; trimethylallylphosphite; tricyclohexylphosphite; triphenylphosphite; tri(2-methylphenyl)phosphite; tri(3-methylphenyl)phosphite; tri(4-methylphenyl)phosphite; tri(2,6-dimethylphenyl)phosphite; tri(4-isopropenylphenyl)phosphite; tri-(4-tertbutenylphenyl)phosphite; 2-methoxy-1,3,2-dioxaphosphorinane; 2-methoxy-4-methyl-1,3,2-dioxaphosphorinane; 2-methoxy-5,5-dimethyl-1,3,2-dioxaphosphorinane.

Such an intermediate, which may be separated or not, is caused to react, at a temperature comprised within the range of from 0° to 40° C., in a solvent (such as, e.g., ethyl alcohol, xylene, dimethylsulfoxide, dimethylformamide, and so forth), with a polyamine having the general formula (XVI):

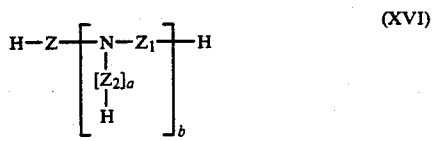

corresponding to one of the structures falling within the scope of the general formula from (II) to (XIII), to yield the intermediate having the general formula (XVII):

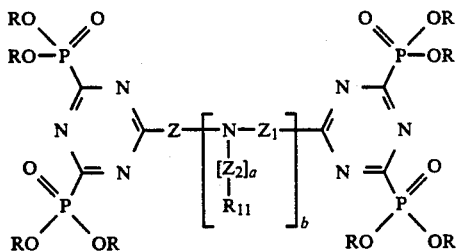

wherein R₁₁ is either hydrogen, or:

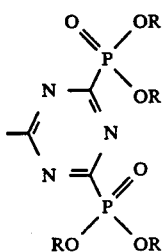

and its meaning may very within each repeating unit.

Such an intermediate, which may be separated, or less, is subsequently caused to react, under analogous conditions to the preceding ones, with an amine having the general formula (XVIII):

 (XVIII)

wherein: R₁ and R₂ have the same meaning as defined hereinabove, with the derivative of general formula (I) being obtained.

An alternative route for the synthesis consists, obviously, in causing the intermediate (XV) to react first with the amine (XVIII) and then with the polyamine (XVI).

The intermediate of general formula (XVII) can alternatively be prepared by causing the cyanuric halide, e.g., cyanuric chloride, to react first with the polyamine having the general formula (XVI), to yield the intermediate of general formula (XIX):

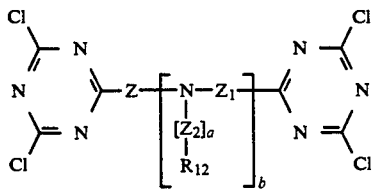

wherein R₁₂ is either hydrogen or:

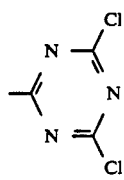

and its meaning may vary within each repeating unit, and subsequently the intermediate of general formula (XIX) to react with the phosphite having the general formula (XIV).

A further alternative route consists in causing the cyanuric halide to react with the amine of general formula (XVIII) to yield the intermediate of general formula (XX):

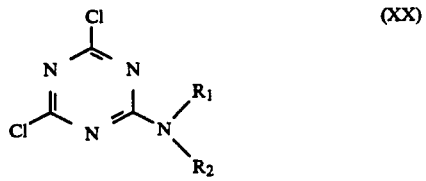

which is subsequently reacted with the phosphite of general formula (XIV), with the intermediate of general formula (XXI) being obtained:

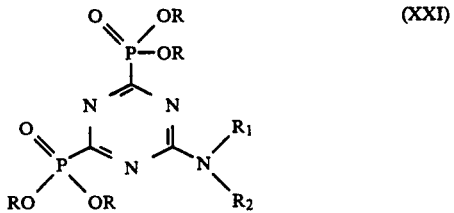

which, in its turn, is caused to react with the polyamine of general formula (XVI).

From the compounds of general formula (I) in which the radicals R are different from hydrogen (preferably C₁-C₂ alkyl), or, taken jointly, form a cycle, the corresponding free acids (in which R is hydrogen and/or hydroxyalkyl) are obtained by means of a hydrolysis reaction.

The reaction of hydrolysis is preferably carried out by using the method described by T. Morita, Y. Okamoto and H. Sakurai, *Bulletin of Chemical Society of Japan* 54, 267-273 (1981), which makes it possible, under very mild conditions, triazinylphosphinic acids to be obtained with a good yield (higher than 70%).

As to that method, for the phosphinic acids of general formula (I), the separation as aniline or cyclohexylamine salts is not necessary, and the hydrolysis may also take place in water.

The phosphonic ester is first reacted with trimethylchlorosilane and sodium or potassium iodide, in order to yield the polykis(trimethylsilyl)phosphonate of general formula (XXII):

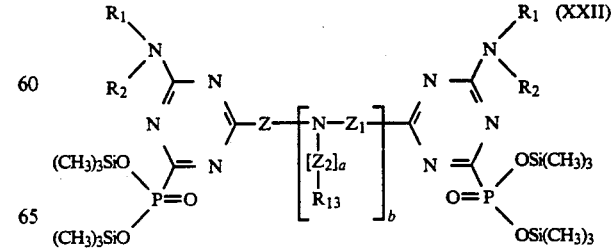

wherein R₁₃ is either hydrogen or:

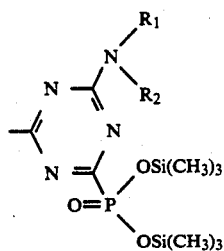

and its meaning may vary inside each repeating unit, at temperature comprised within the range of from 20° to 500° C. in acetonitrile and the intermediate (XXII) is subsequently submitted to a reaction of hydrolysis by treatment with methyl alcohol or water, at temperatures comprised within the range of from 10° to 300° C., to yield the phosphonic acids of general formula (I).

In general, good quality products are obtained as a white crystalline powder, which, as already briefly mentioned, need not be transformed into the corresponding aniline or cyclohexylamine salts in order to be separated.

The product of general formula (I) obtained in that way can be used in the self-extinguishing polymeric compositions without any further purifications.

Derivatives of 2,4-diamino-1,3,5-triazinyl-6-phosphonic acid falling within the scope of general formula (I), not cited in the examples, are those as reported in Table 1, wherein $R_3$, when is present, is replaced by the triazinic ring of formula:

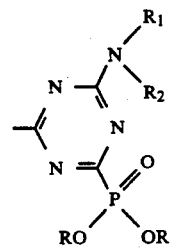

TABLE 1

| PRODUCT N° | R | $R_1$— | N—$R_2$ | $-Z-[N([Z_2]_a)-Z_1-]_b$ |
|---|---|---|---|---|
| 1 | $CH_3$ | $(CH_2)_3OCH_3$ | $(CH_2)_3OCH_3$ | $-HN-(CH_2)_3-NH-$ |
| 2 | phenyl | morpholino (N,O ring) | | piperazine ($-N$, $N-$) |
| 3 | H | piperidino (N ring) | | $-HN-(CH_2)_3-N-(CH_2)_3NH-$ |
| 4 | $CH_3$ | morpholino (N,O ring) | | $-HN(CH_2)_3-N$, $N-(CH_2)_3NH-$ (piperazine) |
| 5 | $C_2H_5$ | $t-C_4H_9$ | H | piperazine ($-N$, $N-$) |
| 6 | $n-C_4H_9$ | thiomorpholino (N,S ring) | | $-HNCH_2CH_2NH-$ |
| 7 | $C_2H_5$ | $CH_2CH_2CH_2N$(morpholino, O) | H | piperazine ($-N$, $N-$) |
| 8 | H | $(CH_2)_4OCH_3$ | H | $-N(CH_3)-CH_2CH_2-N(CH_3)-$ |
| 9 | H | $(CH_2)_2O(CH_2)_2OH$ | H | $-HN-(CH_2)_4-NH-$ |
| 10 | $CH_3$ | $(CH_2)_5OH$ | H | piperazine ($-N$, $N-$) |

TABLE 1-continued $$-Z-\left[N\begin{array}{c}-Z_1\\ |\\ [Z_2]_a\end{array}\right]_b$$

| PRODUCT N° | R | R₁—N—R₂ | | |
|---|---|---|---|---|
| 11 | C₂H₅ | CH₂CH₂OCH=CH₂ | H | —HN—⟨C₆H₄⟩—CONH—⟨C₆H₄⟩—NH— |
| 12 | i-C₃H₇ | CH₂CH₂OCH₃ | H | —NCH₂CH₂NH—<br>    \|<br>  CH₂CH₂OH |
| 13 | H | CH₂CH₂OCH₃ | H | —HN—C(CH₃)₂—⟨cyclohexyl⟩—C(CH₃)₂—NH— |
| 14 | CH₃ | morpholine (N,O ring) | | —HN(CH₂CH₂O)₂CH₂CH₂NH— |
| 15 | C₂H₅ | thiomorpholine (N,S ring) | | —HNCH₂CH₂OCH₂CH₂NH— |
| 16 | H | CH₂CHOH<br>    \|<br>  CH₃ | H | N(CH₂CH₂CH₂NH—)₃ |
| 17 | CH₃ | cyclohexyl | H | piperazine (—N⟨⟩N—) |
| 18 | H | morpholine | | —N—CH₂—CH=CH—CH₂—N—<br> \|                \|<br>C₂H₅            C₂H₅ |
| 19 | cyclohexyl | CH₂CH₂OCH₃ | H | piperazine |
| 20 | CH₃ | (CH₂)₃N(C₂H₅)₂ | H | piperazine |
| 21 | C₂H₅ | (CH₂)₃OH | H | —HNCH₂—⟨cyclohexyl⟩—CH₂NH— |
| 22 | H | morpholine | | —HNCH₂CH₂—N—CH₂CH₂NH—<br>              \|<br>              H |
| 23 | H | morpholine | | —HN—⟨C₆H₄⟩—NH— |

TABLE 1-continued

| PRODUCT N° | R | $R_1-N-R_2$ | | $-Z-\left[\begin{array}{c}N-Z_1\\|\\ [Z_2]_a\end{array}\right]_b$ |
|---|---|---|---|---|
| 24 | CH₃ | CH₂CH₂OCH₃ | CH₂CH₂OCH₃ | 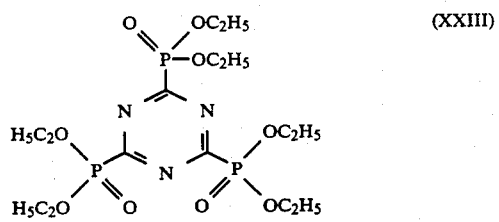 |

The structures of the compounds of general formula (I) reported in the examples were confirmed by NMR analysis.

The examples reported in the following illustrate the features of the invention without limiting them.

EXAMPLE 1

184.5 g of cyanuric chloride and 1 liter of toluene are charged to a reactor of 3 liters of capacity, equipped with stirrer, thermometer, dripping funnel, reflux condenser and heating bath.

The dispersion is stirred at room temperature, then 498.5 g of triethylphosphite are fed during approximately 4 hours.

The reaction is initially exothermic and the temperature reaches the value of 45° C.; then, the temperature is kept at said value of 45° C., by heating the reaction mass from the outside.

When the addition of the reactant is complete, the temperature is increased to 700° C. and the reaction mass is kept at that temperature, with stirring for about 6 hours, until the development of ethyl chloride ceases. A homogeneous solution is obtained.

The solvent is then distilled off; the residue from the distillation of the product, after being cooled down to room temperature, is taken up with 300 cm³ of n-hexane.

The resulting product is filtered and is washed on the fitter with n-hexane.

By drying the fitter cake in a vacuum oven at 700° C., 463.1 g of intermediate (XXIII):

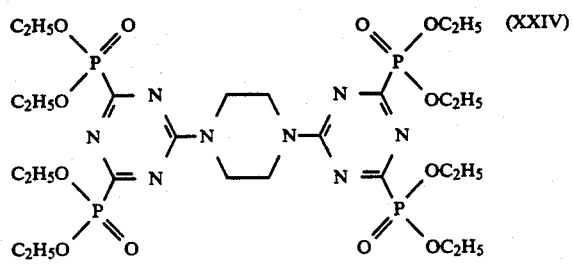

are obtained as a crystalline product having m.p.=91°-94° C. (m.p.=melting point) and containing 19.38% of phosphorus (theoretical value: 19.02%).

400 cm³ of ethyl alcohol, 146.7 g of intermediate (XXIII) and, with stirring, 12.9 g of piperazine are charged to a reactor of 1 liter of capacity, equipped as the preceding one.

The reaction mixture is kept stirred at room temperature for 24 hours.

The solvent is then distilled off and the oil which constitutes the distillation residue is taken up with 300 cm³ of a mixture constituted by n-hexane and ethyl ether in the ratio 1:3.

The product which precipitates is filtered off and is washed on the fitter with the same mixture.

By drying the fitter cake in a vacuum oven, 108.4 g of intermediate (XXIV):

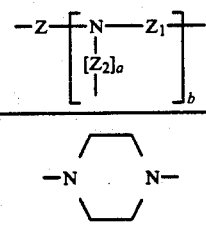

are obtained as a white crystalline powder having m.p.=122°-124° C. and containing 15.61% of phosphorus (theoretical value: 15.74%).

The structure of intermediates (XXIII) and (XXIV) was further confirmed by NMR analysis.

250 cm³ of dimethylsulfoxide and, with stirring, 78.8 g of intermediate (XXIV) and 19.2 g of morpholine are charged to the same reactor of 1 liter of capacity.

The reaction mass is kept with stirring at room temperature for about 40 hours, then the formed product is precipitated by pouring the reaction mixture into 700 g of an ice-water mixture.

The separated product is filtered off and is washed on the fitter with water.

By drying the fitter cake in an oven at 100° C., 55.1 g of the product:

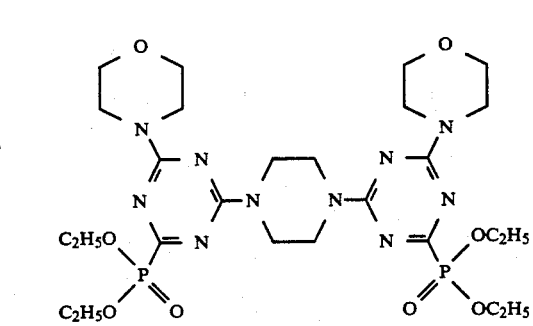

are obtained as a white crystalline powder having m.p.=225°-228° C. and containing 9.16% of phosphorus (theoretical value: 9.04%).

EXAMPLE 2

92.2 g of cyanuric chloride and 300 cm³ of acetone are charged to a reactor of 1 liter of capacity, equipped as in Example 1.

With the reaction mixture being kept cooled from the outside at the temperature of 0°-50° C., during a 1 hour time 21.3 g of piperazine dissolved in 200 cm³ of acetone are added.

Still at the temperature of 0°-50° C., 20 g of sodium hydroxide in 100 cm³ of water are added.

The resulting product is filtered off and is washed on the fitter with the same mixture.

By drying the fitter cake in a vacuum oven at 60° C., 62.3 g of product:

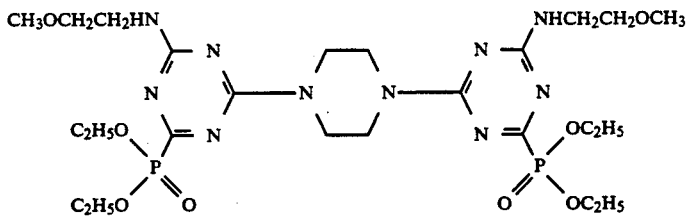

The reaction mixture is kept stirred at 50° C. for a further 4 hours, then 200 cm³ of cold water are added, the formed precipitate is filtered and is washed on the fitter with water.

After drying, 88.7 g of intermediate (XXV):

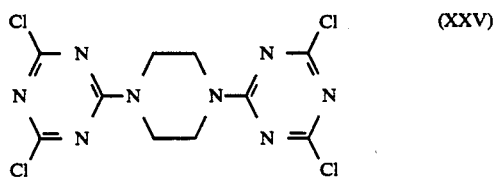

are obtained as a white crystalline powder having a higher m.p. than 300° C., and containing 37.4% of chlorine (theoretical value: 37.2%).

The structure of intermediate (XXV) was confirmed by IR spectroscopic analysis.

To a reaction equipment of 2 liters of capacity equipped as in Example 1, 700 cm³ of Xylene, 76.4 g of intermediate (XXV) and 146.1 g of triethylphosphite are charged.

The temperature of the mixture is gradually increased up to solvent boiling temperature, and the reaction mixture is kept refluxing for about 8 hours.

A portion of the solvent is distilled off and the residue of distillation is first cooled down to room temperature and subsequently treated with 400 cm³ of a mixture constituted by n-hexane/ethyl ether in the ratio 2:1.

The resulting product is filtered off and is washed on the fitter with the same mixture.

By drying in a vacuum oven at 60° C., 123.5 g of intermediate (XXIV) are obtained as a slightly coloured crystalline product having m.p.=120°-123° C. and containing 15.36% of phosphorus (theoretical value: 15.74%).

The structure of the intermediate was confirmed by NMR analysis.

To the same reactor of 1 liter of capacity as used previously, 250 cm³ of dimethylsulfoxide, 78.8 g of intermediate (XXIV) and 15.0 g of 2-methoxyethylamine are charged.

The mixture is kept stirred at room temperature for about 40 hours, then the reaction solution is added to 400 g of an ice-water mixture. The product does not precipitate, so it is extracted with 4 portions of ethyl acetate, each portion being of 200 cm³. The organic extracts are thoroughly dried and the solvent is distilled off.

A thick oil is obtained which, when treated with 300 cm³ of a mixture constituted by ethyl ether/n-hexane in the ratio 3:1, yields a white precipitate.

are obtained as a white crystalline powder having m.p.=145°-147° C. and containing 9.31% of phosphorus (theoretical value: 9.36%).

EXAMPLE 3

To the same reactor of 1 liter of capacity of the preceding example, 450 cm³ of acetonitrile, 41.2 g of the product of Example 1 and 36.0 of sodium iodide are charged.

The mixture is heated to 40° C. and, w i t h t h e temperature being kept at that value, 26.1 g of trimethylchlorosilane are fed during 40 minutes.

The reaction is kept stirred at 40° C. for a further 2 hours, then is cooled to room temperature and the reaction mass is filtered, in order to remove sodium chloride formed during the reaction; the residue is washed on the fitter with acetonitrile.

The solvent is distilled off under reduced pressure, at about 40° C., and the distillation residue is treated with 200 cm³ of methyl alcohol at room temperature.

The resulting product is filtered off and is washed on the fitter with methyl alcohol.

By drying the fitter cake in an oven at 100° C., 31.7 g of the product:

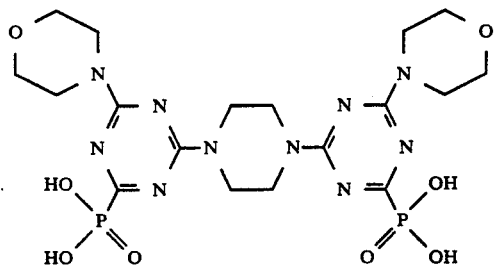

are obtained as a white crystalline powder having a higher m.p. than 300° C., and containing 10.26% of phosphorus (theoretical value: 10.78).

EXAMPLE 4

700 cm³ of ethyl alcohol, 146.7 of intermediate (XXIII) of Example 1 and, with stirring, 26.1 g of morpholine, are charged to a reactor of 2 liters of capacity, equipped as in the preceding example.

The mixture is kept stirred at room temperature for 3 hours.

The solvent is then distilled off and the oil which constitutes the distillation residue is taken up with 500 cm³ of a mixture constituted by n-hexane and ethyl ether in the ratio 1:4.

The separated product is filtered and is washed on the fitter, with the same mixture.

By vacuum drying, 126.9 of intermediate (XXVI):

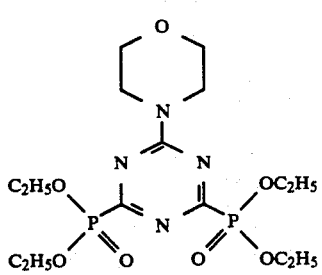

are obtained as a crystalline product having m.p. = 73°-75° C. and containing 13.82% of phosphorus (theoretical value: 14.15%).

The structure of intermediate (XXVI) was confirmed by NMR analysis.

250 cm³ of N,N-dimethylformamide, 87.6 g of intermediate (XXVI) and 6.0 g of ethylenediamine are charged to a reactor of 0.5 l of capacity, equipped as the preceding one.

The reaction mixture is kept stirred at room temperature for 42 hours, and then the process is continued according to the same operating modalities as disclosed in Example 1.

55.3 g of the product:

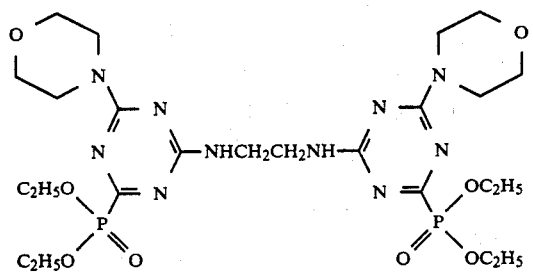

are obtained as a white crystalline powder having m.p. = 203°-207° C. and containing 9.17% of phosphorus (theoretical value: 9.39%).

EXAMPLE 5

800 cm³ of toluene and 110.7 g of cyanuric chloride are charged to the same reactor of 2 liters of capacity of Example 1.

The dispersion is heated to 80° C. and during approximately 2 hours, 224 g trimethylphosphite are fed. The development of methyl chloride starts immediately. The reaction mixture is kept stirred at 80° C. for a further hour, then is heated to its boiling temperature and is kept refluxing for about 1 hour, until the development of methyl chloride ceases. A homogeneous solution is obtained.

The reaction mixture is allowed to coot to room temperature; a precipitate forms as white crystals. The reaction mixture is further cooled to 5° C., the product is filtered off and is washed on the fitter firstly with xylene and then with n-hexane.

By drying the fitter cake in a vacuum oven at 70° C., 233.8 g of the intermediate (XXVII):

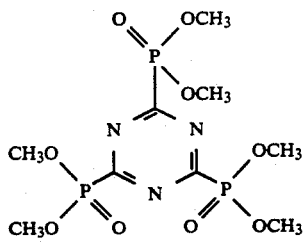

are obtained as a white crystalline powder having m.p. = 119°-122° C. and containing 22.77% of phosphorus (theoretical value: 22.96%).

400 cm³ of ethyl alcohol, 101.2 of intermediate (XXVII) and, with stirring, 10.6 g of piperazine are charged to a reactor of 1 liter of capacity, equipped as the preceding one.

The reaction is kept stirred at room temperature for 20 hours.

The solvent is then distilled off and the distillation residue is taken up with 250 cm³ of a mixture constituted by n-hexane and ethyl ether in the ratio 1:3.

The formed product is filtered off and is washed on the fitter with the same mixture.

By drying the fitter cake in a vacuum oven, 75.7 g of intermediate (XXVIII):

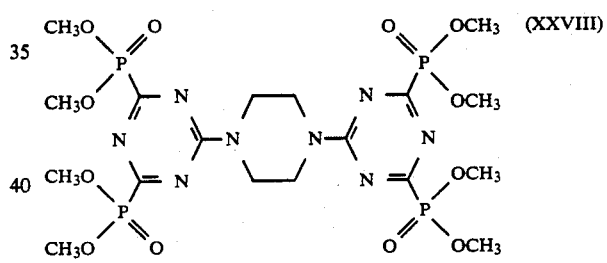

are obtained as a white crystalline powder having m.p. = 164°-168° C. and containing 18.06% of phosphorus (theoretical value: 18.34%).

The structure of intermediates (XXVII) and (XXVIII) was further confirmed by NMR analysis.

400 cm³ of anhydrous ethyl alcohol and 67.6 g of intermediate (XXVIII) are charged to the same reactor of 1 liter of capacity, but now equipped with a cooling bath.

The reaction mixture is stirred until a solution is obtained, then the solution is cooled to 0°-3° C. from the outside, and the solution is saturated with ammonia gas.

The temperature is allowed to rise to 10°-15° C. and the reaction is kept stirred for about 20 hours.

A portion of the solvent is distilled off at room temperature under reduced pressure, and a precipitate is formed.

The product is filtered off and is washed with ethyl alcohol on the fitter.

By oven drying at 100° C., 41.1 g of product:

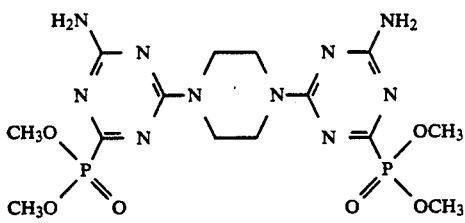
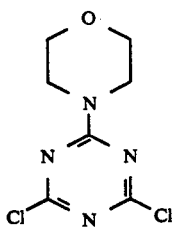

are obtained as a white crystalline powder having a higher m.p. than 300° C., and containing 12.15% of phosphorus (theoretical value: 12.65%).

EXAMPLE 6

500 cm³ of acetonitrile, 39.2 g of the product of Example 5 and 48.0 g of sodium iodide are charged to the same reactor of 1 liter of capacity as of the preceding example.

The mixture is heated to 40° C. and, at such a temperature, 34.7 of trimethylchlorosilane are charged within a 1 hour time.

The mixture is kept at 40° C. for a further 4 hours.

In this case, the silyl ester is insoluble in acetonitrile, so the reaction mixture is filtered, with both the resulting product and sodium chloride formed being separated.

The residue is treated with 300 cm³ of water at room temperature, with sodium chloride being thereby dissolved and the silyl ester being hydrolysed.

The mixture is kept stirred at room temperature for about 4 hours, then the resulting product is filtered off and is washed with water on the fitter.

By oven drying the fitter cake at 100° C., 30.8 g of product:

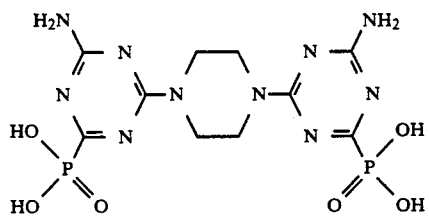

are obtained as a white crystalline powder having a higher m.p. than 300° C., and containing 14.03% of phosphorus (theoretical value: 14.28%).

EXAMPLE 7

To the same reaction apparatus of 3 liters of capacity as of Example 1, but initially provided with a cooling bath, 184.5 g of cyanuric chloride and 1300 cm³ of methylene chloride are charged.

While cooling from the outside, 87.2 g of morpholine and 40 g of sodium hydroxide dissolved in 150 cm³ of water are charged simultaneously during 3 hours, with the pH value being kept comprised within the range of from 5 to 7, and the temperature being kept comprised within the range of from 0° to 3° C.

The temperature is kept at 0°-3° C. for a further 3 hours, then the aqueous phase is separated.

By distilling off methylene chloride, 230 g of intermediate (XXIX):

are obtained as a white crystalline powder having m.p. 155°-157° C.; purity higher than 98% (as determined by gaschromatography) and containing 29.87% of chlorine (theoretical value: 30.21%).

310 g of phosphorus trichloride and, at room temperature and with stirring, during 4 hours, a solution constituted by 208 g of 2,2-dimethyl-1,3-propanediol and 480 cm³ of chloroform are charged to a reactor of 2 liters of capacity, equipped as the preceding one and under nitrogen atmosphere. A constant development of hydrogen chloride occurs.

The reaction mixture is kept stirred for a further 2 hours, until the development of hydrogen chloride ends, then the solvent and unreacted phosphorus trichloride are distilled off. The residual product, consisting of 408 g of a thick liquid, is submitted to a further fractional distillation, and at 60° C. and 10 mmHg, 293.5 g of intermediate (XXX):

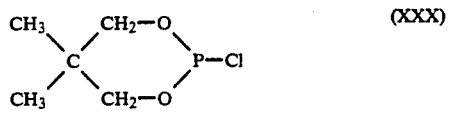

containing 20.98% of chlorine (theoretical value: 21.07%) and 18.31% of phosphorus (theoretical value: 18.40%) are obtained.

To the same reactor of 2 liters of capacity, 800 cm³ of ethyl ether and 286.4 g of intermediate (XXX) are charged.

The reaction mixture is cooled to 5° C. from the outside, and, with the temperature being kept comprised within the range of from 5° to 7° C., a solution constituted by 340 cm³ of ethyl ether, 142.0 of pyridine and 54.4 of methyl alcohol is charged during approximately 1 hour.

When the addition is complete, the temperature is allowed to increase to room temperature, and the reaction is kept stirred for 1 hour, then is heated to boiling temperature and is kept refluxing for a further hour.

The reaction mixture is cooled down to 15° C. and then is filtered in order to separate pyridine chloride formed; the fitter cake is washed on the fitter with a little of ethyl ether.

The solvent is distilled off and a residue is obtained, which consists of 316 g of a liquid which is submitted to fractional distillation.

The fraction boiling at 62°-64° C. and 17 mmHg is collected. It is constituted by 254.8 g of the intermediate (XXXI):

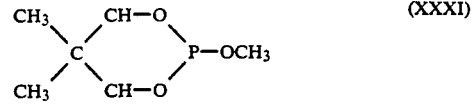

having the appearance of a colourless liquid containing 18.81% of phosphorus (theoretical value: 18.90%).

480 cm³ of orthodichlorobenzene, 141.2 of intermediate (XXIX) and 216.8 g of intermediate (XXXI) are charged to a reactor of 1 liter of capacity, equipped as in the preceding examples.

The mixture is heated to 160° C.; at about 140° C., the development of methyl chloride starts.

filtered off and is washed on the fitter with a little of solvent.

The fitter cake is treated, inside the same reactor, with 400 cm³ of water, and is kept stirred for 30 minutes.

The product is filtered off once more and is washed with water on the fitter.

By oven drying the fitter cake at 80° C., 68.8 of product:

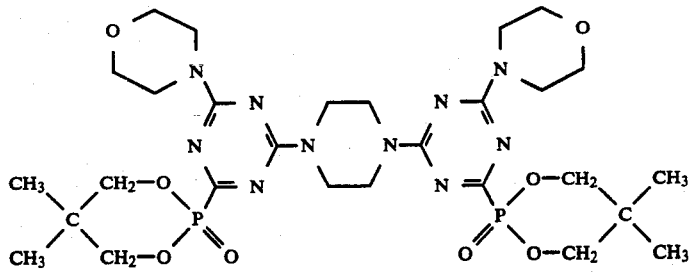

The reaction mixture is kept at 160° C. for 6 hours, until the development of methyl chloride ends.

The reaction mixture is allowed to coot down to room temperature and a precipitate is formed.

The product is filtered off and is washed on the fitter with orthodichlorobenzene. The fitter cake is taken up, inside the same reactor, with 400 cm³ of n-hexane, and is kept with stirring for 30 minutes.

The product is filtered off once more, and is washed on the fitter with n-hexane.

By oven drying the fitter cake at 100° C., 222.3 g of intermediate (XXXII):

(XXXII)

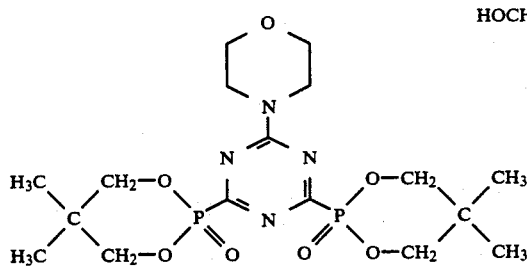

are obtained as a white crystalline powder having m.p.=236°-240° C. and containing 13.20% of phosphorus (theoretical value: 13.42%).

The structure of intermediate (XXXII) was confirmed by NMR analysis.

400 cm³ of dimethylsulfoxide, 115.5 g of intermediate (XXXII) and 10.7 g of piperazine are charged to a reactor of 1 liter of capacity equipped as the preceding ones.

The reaction mixture is kept 46 hours with stirring at room temperature, and then the separated product is are obtained as a white crystalline powder having m.p.=280°-285° C. and containing 8.47% of phosphorus (theoretical content: 8.73%).

EXAMPLE 8

250 cm³ of water, 13.4 g of sodium hydroxide and 56.8 g of the product of Example 7 are charged to a reactor of 0.5 l of capacity, equipped as in the preceding examples.

The reaction mass is heated to 85° C. and is kept 1 hour with stirring at that temperature.

The temperature is decreased to room temperature and the PH value is adjusted at 5-6 by means of the addition of an aqueous solution of hydrochloric acid.

The resulting product is filtered off and is washed with water on the fitter.

By oven drying the fitter cake at 100° C., 57.1 g of the product:

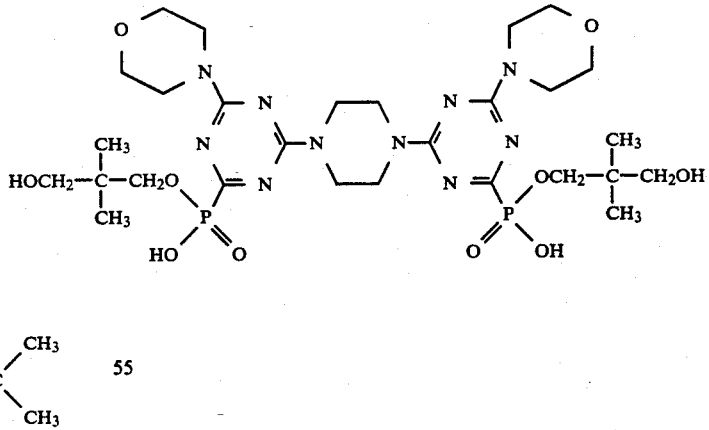

are obtained as a white crystalline powder having a higher m.p. than 300° C. and containing 8.12% of phosphorus (theoretical content: 8.31%).

EXAMPLES 9-14

By operating under analogous conditions to as disclosed in Examples from 1 to 8, the products of general formula (I) reported in Table 2 are prepared. In such a structure, R₃, when is present, is replaced by the triazinic ring of formula;

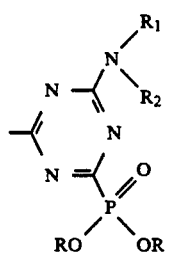

We claim:
1. A derivative of 2,4-diamino-1,3,5-triazinyl-6-phosphonic acid of the formula (I):

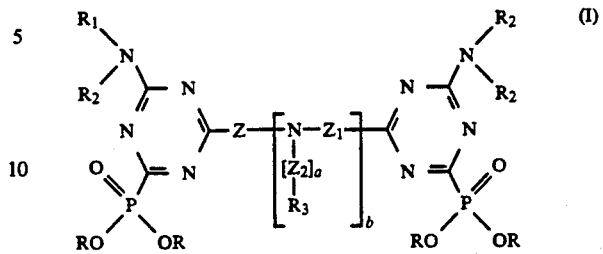

TABLE 2

| EXAMPLE No. | R | $R_1-N-R_2$ | $-Z-[N(-[Z_2]_a)-Z_1-]_b$ | Phosphorus % Calculated | Found | m.p. (°C.) |
|---|---|---|---|---|---|---|
| 9 | H | (N–S ring, thiomorpholine) | $-HNCH_2CH_2-N(-)-CH_2CH_2NH-$ | 10,53 | 10,16 | >300 |
| 10 | H | (N–N–CH$_3$ ring, N-methylpiperazine) | $-HN-(CH_2)_6-NH-$ | 9,84 | 10,07 | >300 |
| 11 | $C_2H_5$ | $CH_2CH_2OH$   H | $-N(\quad)N-$ (piperazine) | 9,78 | 9,47 | 145–149 |
| 12 | H | (piperidine N) | $-N(\quad)N-$ (piperazine) | 10,88 | 10,71 | >300 |
| 13 | $CH_3$ | $CH_2-CH=CH_2$   H | $-N(CH_3,CH_3)N-$ (2,6-dimethylpiperazine) | 10,37 | 10,02 | 242–246 |
| 14 | H | (morpholine N–O) | $HNCH_2-$ (cyclohexyl) $-CH_2NH-$ | 9,84 | 9,51 | >300 |

EXAMPLE 15

75.0 g of isotactic polypropylene flakes, having a Melt Flow Index equal to 12 and containing 96% by weight of a fraction insoluble in n-heptane; 12.0 g of the product of Example 1; 12.0 g of ammonium polyphosphate (Exolit 422 ex Hoechst); 0.67 g of dilauryl thiopropionate and 0.33 g of pentaerythritol tetra[3-(3,5-di-tert-butyl-4-hydroxyphenyl)propionate] are blended and moulded on a MOORE platen press, by operating for 7 minutes at a pressure of 40 kg/cm².

Specimens are obtained as small slabs of approximately 3 mm of thickness, and on them the level of self-extinguishment is determined by measuring the oxygen index (L.O.I. according to ASTM D-2863/77) on a STANTON REDCROFT instrument, and applying the "Vertical Burning Test", which makes it possible the material to be classified at the three levels 94 V-0/ 94 V-1 and 94 V-2 according to UL 94 standards (published by "Underwriters Laboratories"—USA).

The following results are obtained:
L.O.I. = 35.8
UL 94 (3 mm) = Class V-0.

wherein:
the radicals R, which can be the same, or different from each other, are: hydrogen; $C_1$–$C_5$ alkyl; $C_3$–$C_5$ hydroxyalkyl; $C_3$–$C_4$ alkenyl; cyclohexyl; $C_6$–$C_{10}$ aryl; $C_7$–$C_8$ aralkyl; or, taken jointly, can constitute a cyclic structure, as:

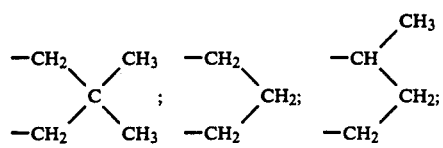

the radicals $R_1$ and $R_2$, which can be the same, or different from each other, and which can have different meanings on each triazinic ring, are: H; $C_1$–$C_{18}$ alkyl; $C_2$–$C_8$ alkenyl; $C_6$–$C_{16}$ cycloalkyl or alkylcycloalkyl;

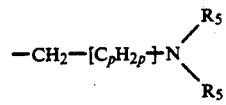

wherein:
m is an integer comprised within the range of form 1 to 7;
p is an integer comprised within the range of from 1 to 5;
$R_4$ is H; $C_1$–$C_8$ alkyl; $C_2$–$C_6$ alkenyl; $-(C_qH_{2q})-O-R_6$ wherein q is an integer comprised within the range of from 1 to 4 and $R_6$ is H or $C_1$–$C_4$ alkyl; $C_6$–$C_{12}$ cycloalkyl or alkylcycloalkyl;
the radicals $R_5$, which can be the same, or different from each other, are H; $C_1$–$C_8$ alkyl; $C_2$–$C_6$ alkenyl; $C_6$–$C_{12}$ cycloalkyl or alkylcycloalkyl; $C_1$–$C_4$ hydroxyalkyl; or the moiety:

is replaced by a heterocyclic radical selected from the group consisting of aziridine, pyrrolidine, piperidine, morpholine, thiomorpholine, piperazine, 4-methylpiperazine, 4-ethylpiperazine, 2-methylpiperazine, 2,5-dimethylpiperazine, 2,3,5,6-tetramethylpiperazine, 2,2,5,5-tetramethylpiperazine, 2-ethylpiperazine, and 2,5-diethylpiperazine;
or in the general formula (I) the moiety:

is replaced by a heterocyclic radical selected from the group consisting of aziridine, pyrrolidine, piperidine, morpholine, thiomorpholine, piperazine, 4-methylpiperazine, and 4-ethylpiperazine;
a is 0 or 1;
b is 0 or an integer comprised within the range of from 1 to 5;
$R_3$ is hydrogen or:

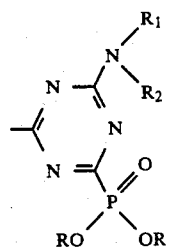

and its meaning may vary within each repeating unit;

when b is 0, Z is a divalent radical falling within the scope of one of the following formulae:

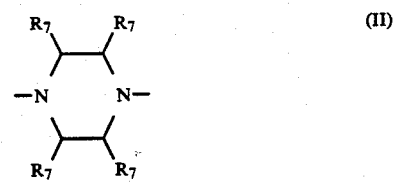 (II)

wherein the radicals $R_7$, which may be the same or different from each other, are hydrogen or $C_1$–$C_4$ alkyl;

 (III)

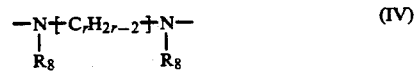 (IV)

wherein r is an integer comprised within the range of from 2 to 14; $R_8$ is hydrogen; $C_1$–$C_4$ alkyl; $C_2$–$C_6$ alkenyl; $C_1$–$C_4$ hydroxyalkyl;

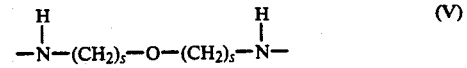 (V)

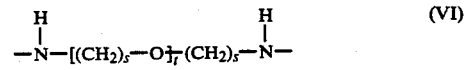 (VI)

wherein s is an integer comprised within the range of from 2 to 5 and t is an integer comprised within the range of from 1 to 3;

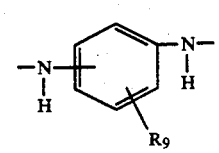 (VII)

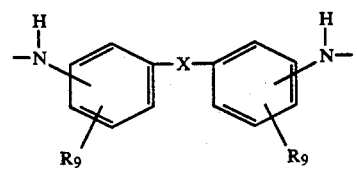 (VIII)

wherein:
X is a direct C—C bond; O; S; S—S; SO; $SO_2$; NH; $NHSO_2$; NHCO; N=N; $CH_2$;
$R_9$ is hydrogen; hydroxy; $C_1$–$C_4$ alkyl; $C_1$–$C_4$ alkoxy;

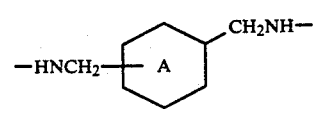 (IX)

wherein A can be saturated or unsaturated ring;

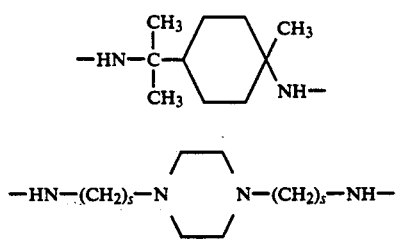

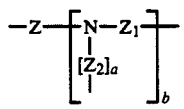

wherein s has the above defined meaning;
when, on the contrary, b is an integer comprised within the range of from 1 to 5, the moiety;

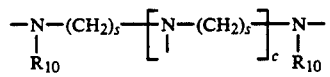

is a multivalent radical falling within the scope of one of the following formulae:

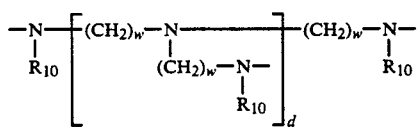

wherein:
$R_{10}$ is hydrogen or $C_1$–$C_4$ alkyl;
c is an integer comprised within the range of from 1 to 5;
the indexes s, which can be the same, or different from each other, have the same meaning as defined hereinabove;

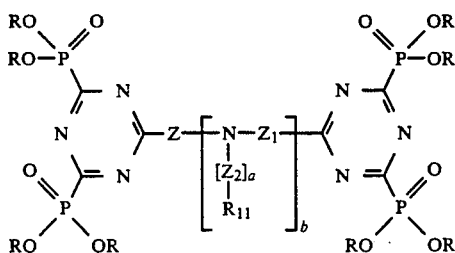

wherein:
$R_{10}$ has the same meaning as defined hereinabove;
w is an integer comprised within the range of from 2 to 4;
d is either 1 or 2.

2. A process for preparing said derivative of 2,4-diamino-1,3,5-triazinyl-6-phosphonic acid having the general formula (I) according to claim 1, wherein said derivative is obtained by reacting an intermediate of the formula (XVII):

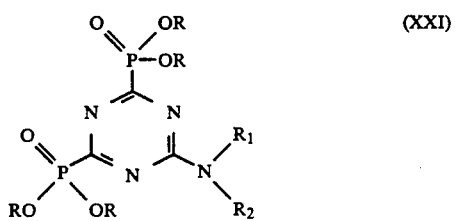

wherein the radicals R, different from H and $C_3$–$C_5$ hydroxyalkyl, having the meaning defined in claim 1, and $R_{11}$ is either hydrogen, or:

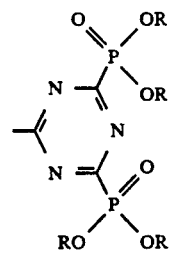

and its meaning may vary within each repeating unit; with an amine having the general formula (XVIII):

wherein $R_1$ and $R_2$ have the same meaning as defined in claim 1.

3. A process for preparing said derivative of 2,4-diamino-1,3,5-triazinyl-6-phosphonic acid having the general formula (I) according to claim 1, wherein said compound is obtained by reacting a polyamine of the formula (XVI):

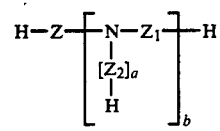

corresponding to one of the general formulae from (II) to (XIII), defined in claim 1, with an intermediate of general formula (XXI):

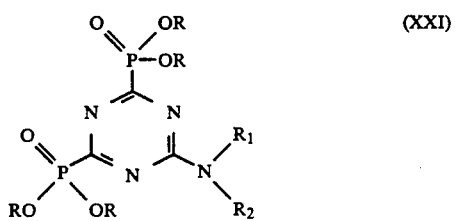

wherein the radicals R, different from hydrogen and $C_3$–$C_5$ hydroxyalkyl, have the meaning defined in claim 1.

4. The process according to claim 3, in which the hydrolysis reaction is carried out by reacting said derivative of the formula (I) in which R is $C_1$–$C_2$ alkyl, with trimethylchlorosilane, in order to yield a polykis(trimethylsilyl)phosphonate of the formulate (XXII):

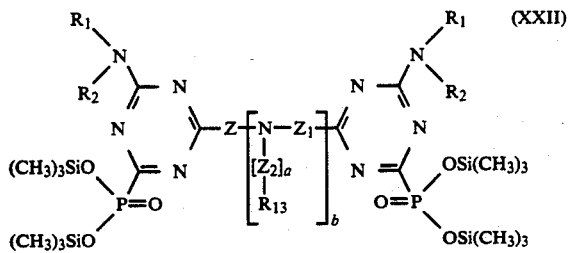

wherein $R_{13}$ is either hydrogen or:

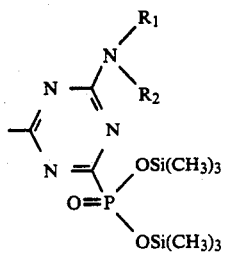

and its meaning can vary inside each repeating unit, and subsequent treatment of said intermediate (XXII) with methyl alcohol or water.

5. The process according to claim 2 or 3, in which said reaction between said intermediate of the formula (XVII) and said amine of the formula (XVIII), or said reaction between said polyamine of the formula (XVI) and said intermediate of the formula (XXI), is carried out in a solvent selected from the group consisting of ethyl alcohol, xylene, dimethylsulfoxide and dimethylformamide, at a temperature comprised within the range of from 0° to 40° C.

6. The process for preparing said derivative of 2,4-diamino-1,3,5-triazinyl-6-phosphonic acid of the formula (I) according to any of claims from 2 to 4, in which R is hydrogen, wherein said derivative is obtained by hydrolyzing the corresponding derivative in which R is different from hydrogen, and preferably is a $C_1$–$C_2$ alkyl.

7. The process according to claim 4, wherein said reaction with trimethylchlorosilane is carried out in the presence of acetonitrile at a temperature comprised within the range of from 20° to 50° C. and the subsequent reaction of said intermediate of the formaul (XXII) is carried out with methyl alcohol or water at a temperature comprised within the range of from 10° to 30° C.

* * * * *

UNITED STATES PATENT AND TRADEMARK OFFICE
CERTIFICATE OF CORRECTION

PATENT NO.   :   5,296,598
DATED        :   March 22, 1994
INVENTOR(S)  :   Roberto CIPOLLI, et al.

It is certified that error appears in the above-indentified patent and that said Letters Patent is hereby corrected as shown below:

On the title page, Item [73], the Assignee's name should read as follows:

--Ministero Dell 'Universita' E Della Ricerca Scientifica E Tecnologica, Rome, Italy--

Signed and Sealed this

Twenty-sixth Day of July, 1994

Attest:

BRUCE LEHMAN

*Attesting Officer*          *Commissioner of Patents and Trademarks*